United States Patent

Brimhall

[11] Patent Number: 5,913,845
[45] Date of Patent: Jun. 22, 1999

[54] NEEDLE PULLER/CATHETER ADAPTOR COUPLING DEVICE

[75] Inventor: Greg L. Brimhall, West Jordan, Utah

[73] Assignee: Becton, Dickinson and Company, Franklin Lakes, N.J.

[21] Appl. No.: 08/898,888

[22] Filed: Jun. 2, 1997

[51] Int. Cl.⁶ .................................................. A61M 5/178
[52] U.S. Cl. .......................................... 604/165; 604/164
[58] Field of Search .................................... 604/164, 165, 604/166, 264, 272, 158

[56] References Cited

U.S. PATENT DOCUMENTS 5,501,675  3/1996  Erskine .................................. 604/263

Primary Examiner—Wynn Wood Coggins
Assistant Examiner—N. Kent Gring
Attorney, Agent, or Firm—Eric M. Lee

[57] ABSTRACT

Disclosed is a yoke latch for coupling a needle puller and a catheter adaptor of a vascular access device. The yoke latch generally comprises a push bar, at least one prong attached to the push bar, and at least one locking tab attached to the prong. The yoke latch is generally horseshoe-shaped and straddles the needle puller. When the needle puller and catheter are joined, the locking tab of the yoke latch engage the catheter adaptor preventing its movement relative to the needle puller. A clinician, therefore, can grip the vascular access device by the catheter adaptor, or any part thereof, for better control without having the catheter prematurely uncouple from the needle puller during catheter insertion. The yoke latch also permits one hand yoke latch disengagement and needle puller removal.

3 Claims, 2 Drawing Sheets

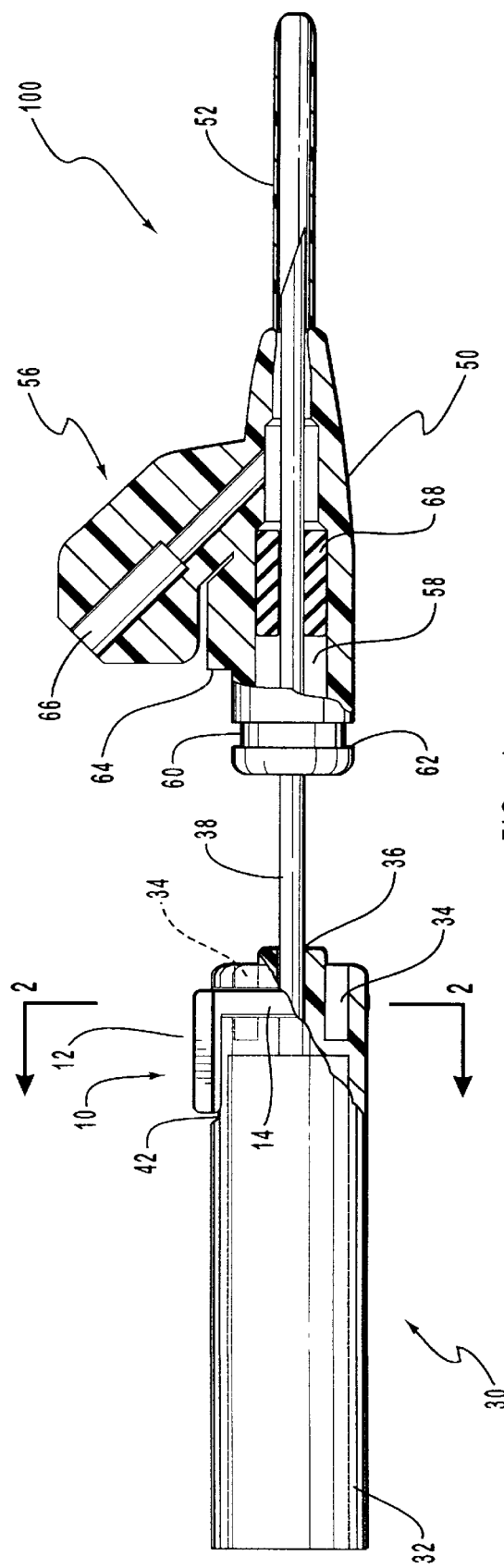
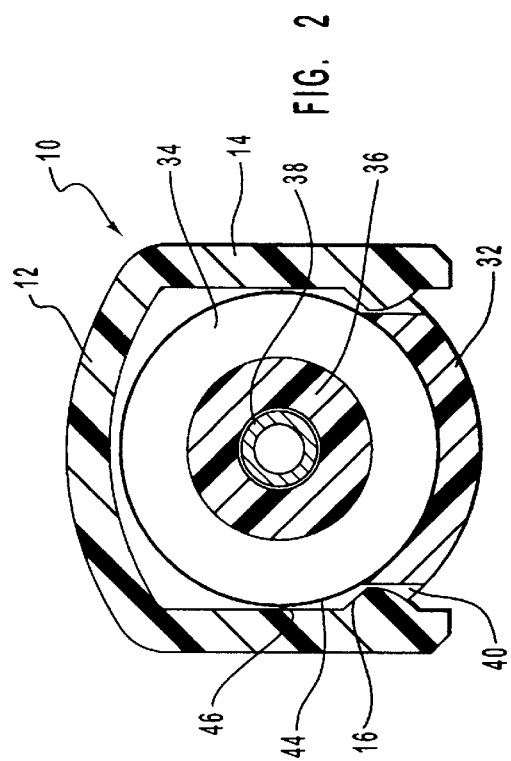

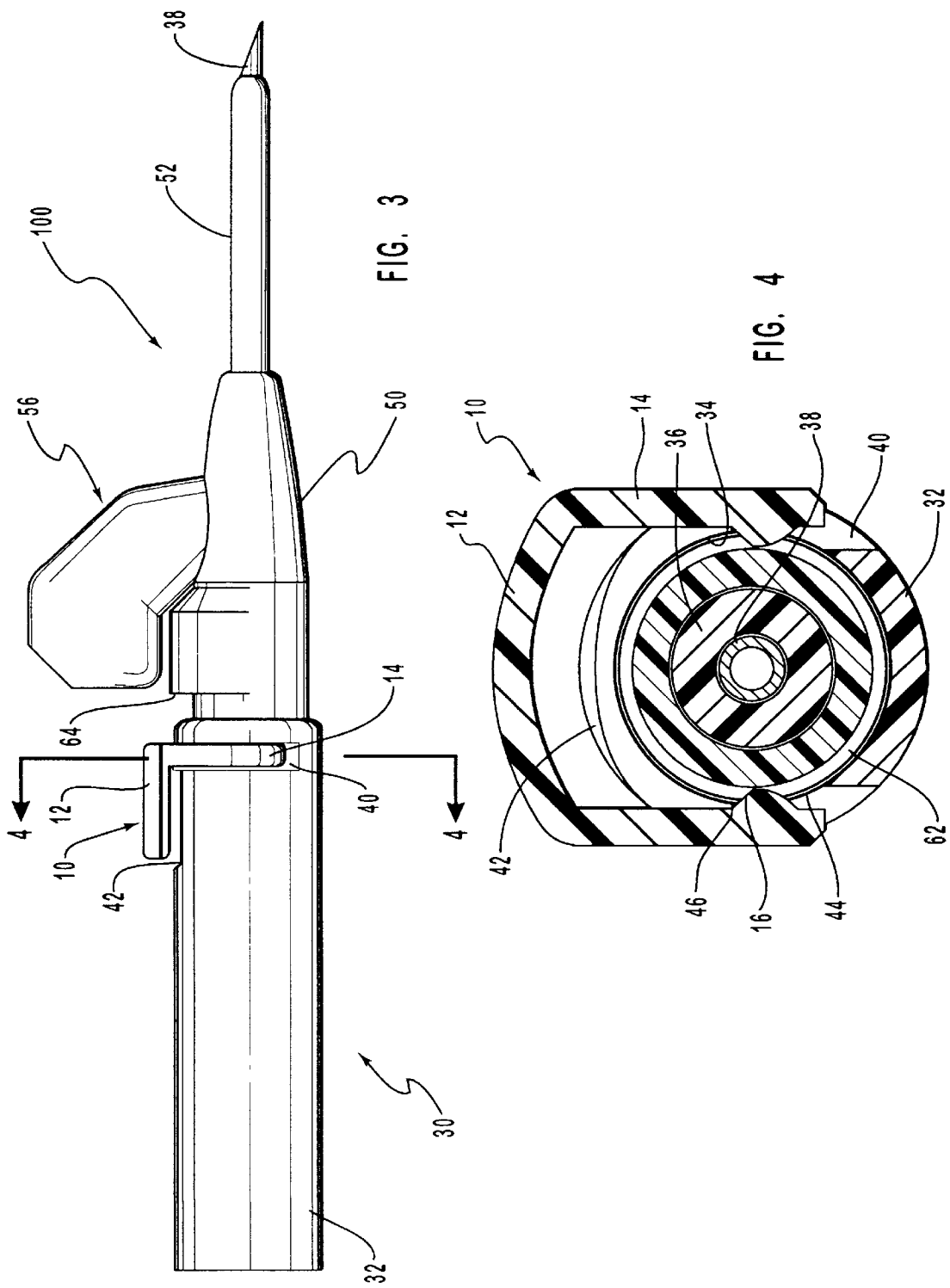

NEEDLE PULLER/CATHETER ADAPTOR COUPLING DEVICE

1. THE FIELD OF THE INVENTION

The present invention relates to a device for coupling a needle puller and a catheter of a vascular access device. More particularly, the present invention relates to a yoke latch which allows a clinician to grip a vascular access device by catheter adaptor for better control without having the catheter prematurely uncouple from the needle puller during catheter insertion.

2. BACKGROUND

During medical treatment, patients often require medication, blood, and fluids. The most efficient way of administering these substances is by depositing them directly into the patient's blood stream where the circulatory system quickly directs the substance to the target tissue or organ. Administering a substance directly into a patient's blood stream is most commonly accomplished by injection with a conventional needle and syringe. During the course of treatment, however, a patient will often require repeated or continuous doses of medications. It will be appreciated that repeated injections with conventional syringes can damage blood vessels and cause significant discomfort to the patient.

Therefore, when a patient requires repeated doses of medication or other substances, catheters are commonly used in the health care profession. In one common configuration, a catheter comprises a catheter adaptor and a hollow tubular cannula. The catheter adaptor and cannula are usually constructed from a single mold such that a continuous fluid passage extends from the catheter adaptor to the catheter cannula. When the catheter is in use, the hollow tubular cannula is disposed within the patient's blood vessel, while the catheter adaptor remains outside where it can be accessed by medical personnel. A medication, blood, or fluid container is securely attached to the catheter adaptor. The substance in the container flows through the continuous fluid passage in the catheter and directly into the patient's blood vessel. As such, the patient receives a continuous supply of medication, blood, or fluid without repeated injections with conventional needles and syringes.

Typically, a vascular access device is used to insert a catheter within a patient's blood vessel. A vascular access device generally comprises a needle puller, an introducer needle, and a catheter. The needle puller is used to grip the vascular access device during catheter insertion. The sharp introducer needle having a beveled tip is attached to the end of the needle puller and used to pierce the patient's skin and access the patient's blood vessel. The catheter concentrically fits over the introducer needle through the continuous fluid passage in the catheter and is held in place by friction engagement between the catheter adaptor and the needle puller. The catheter is usually constructed of a pliable material that will not irritate the inner wall of the blood vessel or unduly limit the patient's movement.

The introducer needle is longer than the catheter cannula. Therefore, when the catheter adaptor is properly attached to the needle puller, the beveled tip of the introducer needle extends beyond the end of catheter cannula. It is important that the introducer needle extend beyond the catheter cannula so that during catheter insertion the introducer needle is available to pierce the patient's skin and access the blood vessel. It will be appreciated that because the catheter is made of a pliable material, unless the introducer needle first pierces the patient's skin and blood vessel, the catheter cannula cannot be inserted into the patient's blood vessel.

In use, a clinician, while gripping the needle puller, pierces the patient's skin with the introducer needle and locates the patient's blood vessel. Once the introducer needle is in the patient's blood vessel, the clinician detaches the catheter adaptor from the needle puller. The catheter cannula is then inserted into the patient's blood vessel by sliding it along the introducer needle until the desired length of the cannula is within the blood vessel. Once the catheter cannula is in place, the introducer needle is removed by slowing pulling back on the needle puller, leaving the catheter cannula within the patient's blood vessel. Finally, a medication, blood, or fluid container is attached to the catheter adaptor.

It will be appreciated, however, that for a variety of reasons it is often difficult to locate and successfully insert the introducer needle into the blood vessel of interest. When the blood vessel is small or difficult to locate, clinicians tend to hold the vascular access device by the catheter adaptor rather than the needle puller. Like a baseball player choking on a bat, holding the vascular access device nearer the tip of the introducer needle gives the clinician greater stability and control over the introducer needle. The increased stability and control makes it easier to insert the introducer needle and catheter cannula into the patient's blood vessel.

Unfortunately, conventional vascular access devices do not permit the clinician to grip the vascular access device by the catheter adaptor. Initially, the catheter adaptor is securely attached to the needle puller by friction engagement. The force used to pierce the patient's skin, however, often causes the catheter adaptor to uncouple from the needle puller before the blood vessel has been located and pierced. Once the catheter is uncoupled, the catheter cannula prematurely slides along the introducer needle. The introducer needle, therefore, cannot be advanced further, making it difficult, if not impossible, to insert the pliable catheter cannula into the patient's blood vessel.

From the foregoing, it will be appreciated that it would be an advancement in the art to provide a device that would permit a vascular access device to be gripped by the catheter adaptor. It would be yet another advancement to provide a device for coupling a needle puller to a catheter such that the catheter does not prematurely uncouple from the needle puller during catheter insertion. It would be a further advancement in the art if the coupling device could be easily disengaged once the introducer needle was in the blood vessel and the catheter was ready for insertion into the patient's blood vessel. In would be yet another advancement if the coupling device could be disengaged with one hand. Such a coupling device is disclosed and claimed herein.

3. BRIEF SUMMARY AND OBJECTS OF THE INVENTION

The present invention is for a yoke latch which reversibly couples a needle puller and a catheter of a vascular access device. The device is particularly useful when the patient's blood vessel is small or difficult to locate. The device allows a clinician to grip the vascular access device by the catheter adaptor or cannula for better control without having the catheter adaptor prematurely uncouple from the needle puller.

In one presently preferred embodiment, the vascular access device comprises a needle puller, a catheter, and a yoke latch. The needle puller has a generally cylindrical body used to grip the vascular access device during a typical catheter insertion procedure. The proximal face of the needle puller body, has a doughnut-shaped cavity. A cylindrical stem extends from the center of the cavity. The stem is molded around and secures an introducer needle to the needle puller body. The proximal end of the needle puller body also has a pair of parallel vertical channels. Each channel has a slit which creates an opening into the cavity in the proximate face of the needle puller body.

The catheter fits concentrically over the introducer needle. In one embodiment, the catheter generally comprises a hollow tubular cannula, a catheter adaptor, and optionally a catheter insertion fin. The catheter cannula and catheter adaptor are usually constructed from a single mold. The catheter adaptor has an interior opening which joins with the distal end of hollow tubular catheter cannula creating a continuous fluid flow passage through the catheter. The distal end of the opening in the catheter adaptor is configured to engage with the cavity and stem located on the proximal face of the needle puller. The distal end of the catheter adaptor also has a latch groove. The width of the latch groove is approximately the same width of the channels in the needle puller body. The latch groove carves out a latch groove lip.

Prior to catheter insertion, the needle puller and the catheter are frictionally engaged. The needle puller and catheter adaptor are configured such that the cavity in the proximal face of the needle puller fits over the outer diameter of the catheter adaptor, and the stem of the needle puller fits into the opening in the distal end of the catheter adaptor. When properly engaged, the latch groove in the catheter adaptor is vertically aligned with the channels in the needle puller such that the latch groove and latch groove lip can be accessed through the channels and slits in the needle puller body.

The yoke latch reversibly couples the needle puller and catheter adaptor. In one preferred embodiment, the yoke latch comprises a push bar, a pair of prongs and a pair of locking tabs. The yoke latch is generally horseshoe-shaped with the push bar extending perpendicularly from the crest of the horseshoe. The prongs staddle the needle puller such that the push bar rests on top of the needle puller body and the prongs rest within the channels. The prongs are able to travel vertically using the channels in the needle puller body as a track. The locking tabs extend inwardly from the prongs and, in certain positions along the vertical axis, protrude the cavity in the proximal face of the needle puller body through the slits in the needle puller body channels.

When the yoke latch is in an engaged position, the push bar is elevated above the needle puller. In this position, the locking tabs protrude the cavity in the proximal face of the needle puller body and overlap the catheter latch groove lip, thus preventing the catheter from uncoupling from the needle puller during catheter insertion. Depressing the push bar disengages the yoke latch by positioning the locking tabs such that they no longer overlap the latch groove lip and the catheter can be uncoupled from the needle puller.

In practice, with the yoke latch engaged, the clinician first inserts the introducer needle into the patient's blood vessel. Because the needle puller and the catheter are securely coupled by the yoke latch, if necessary, the clinician can grip the vascular access device by the catheter adaptor. Once the patient's blood vessel has been located, the clinician depresses the push bar, disengaging the yoke latch. The clinician then uncouples the catheter adaptor from the needle puller and slides the catheter along the introducer needle until the desired length of the catheter cannula is within the patient's blood vessel. While holding the catheter in place, the clinician slowly pulls back on the needle puller removing the introducer needle from within the blood vessel. Finally, medication and other fluids can be attached to the catheter adaptor and administered to the patient.

Thus, by securely and reversibly coupling the needle puller and the catheter, the present invention permits a clinician to grip the vascular access device by the catheter adaptor for better control in situations where the patient's blood vessel is difficult to locate. Moreover, the yoke latch of the present invention is easy to use and can be disengaged with one hand.

These and other objects and advantages of the present invention will become more fully apparent by examination of the following description of the preferred embodiments and the accompanying drawings.

4. BRIEF DESCRIPTION OF THE DRAWINGS

A more particular description of the invention briefly described above will be rendered by reference to the appended drawings. These drawings only provide information concerning typical embodiments of the invention, and therefore, are not to be considered limiting of its scope.

The invention will be described and explained with additional specificity and detail through the use of the accompanying drawings, in which:

FIG. 1 is a partial cutaway side view of a vascular access device illustrating the yoke latch of the present invention in a disengaged position.

FIG. 2 is a cross sectional front view of the yoke latch of the present invention in a disengaged position.

FIG. 3 is a side view of a vascular access device illustrating the yoke latch of the present invention in an engaged position.

FIG. 4 is a cross sectional front view of the yoke latch of the present invention in an engaged position.

5. DETAILED DESCRIPTION OF THE PREFERRED EMBODIMENTS

The present invention can be better understood with reference to the figures wherein like parts are referred to by like numerals throughout. As illustrated in FIGS. 1 and 3, the present invention is a yoke latch 10 which securely and reversibly couples a needle puller 30 and a catheter adaptor 50 of a vascular access device 100. Yoke latch 10 prevents needle puller 30 and catheter adaptor 50 from separating during catheter insertion, particularly if the clinician holds vascular access device 100 by catheter adaptor 50 rather than needle puller 30. Once the vascular access device 100 is in position, yoke latch 10 can be easily disengaged, uncoupling needle puller 30 from catheter adaptor 50 and allowing catheter cannula 52 to be inserted into the patient's blood vessel.

FIG. 1 illustrates the present invention when needle puller 30 is uncoupled from catheter adaptor 50 and yoke latch 10 is disengaged. Vascular access device 100 generally comprises a needle puller 30, a yoke 10 and a catheter adaptor 50. Needle puller 30 has a needle puller body 32. Needle puller body 32 is generally cylindrical and used to grip vascular access device 100 during typical catheter insertion procedures. It will be appreciated that the configuration of needle puller body 32 is not critical to the invention. Moreover, needle puller body 32 can be constructed of various materials well known in the art, including plastic, metal, and combinations thereof.

With continued reference to FIG. 1, the proximal face of needle puller body 32, has a doughnut-shaped cavity 34. A cylindrical stem 36 extends from the center of cavity 34. Stem 36 is molded around and secures introducer needle 38 to needle puller body 32. It will be appreciated, however, that introducer needle 38 can be secured to stem 36 by a variety of means including adhesive means. As best illustrated in FIGS. 3 and 4, the proximal end of needle puller body 32 also has a pair of parallel vertical channels 40. Each channel 40 has a slit 44 which creates an opening into cavity 34. For reasons explained in detail below, the width of needle puller body 32 measured between channels 40 is greater above slits 44 and less below slits 44. This disparity in width creates abutments 46.

Yoke latch 10 is located at the proximal end of needle puller body 32. As illustrated in FIGS. 1 and 2, in one embodiment, yoke latch 10 generally comprises a push bar 12, a pair of prongs 14, and a pair of locking tabs 16. Yoke latch 10 is generally horseshoe-shaped with push bar 12 extending perpendicularly from the crest of the horseshoe. Prongs 14 staddle needle puller body 32 and rest within channels 40. Prongs 14 and channels 40 are configured such that prongs 14, and hence yoke latch 10, can travel vertically along channels 40. When yoke latch 10 is disengaged, push bar 12 sits on top of needle puller body 32 which optionally has a recess 42 to accommodate push bar 12, and prongs 14 completely occupy channels 40. As best illustrated in FIG. 2, prongs 14 are dimensioned such that when they are resting within channels 40, prongs 14 are flush with the outer diameter of, and hence do not protrude, cavity 34 of needle puller body 32.

Locking tabs 16 extend inwardly from prongs 14 and toward cavity 34. Slits 44 accommodate locking tabs 16 as prongs 14 travel vertically along channels 40. The maximum upward vertical travel of yoke latch 10 is dictated by abutments 46 which prevents locking tabs 16 from traveling further along slits 44. As illustrated in FIG. 2, locking tabs 16 are located on prongs 14 such that when yoke latch 10 is disengaged, locking tabs 16 do not protrude cavity 34. However, as illustrated in FIG. 4, as yoke latch 10 is raised and becomes engaged, locking tabs 16 travel vertically along slits 44 and protrude cavity 34.

As illustrated in FIGS. 1 and 3, catheter adaptor 50 concentrically fits over introducer needle 38 and engages needle puller 30. Catheter adaptor 50 generally comprises a hollow tubular catheter cannula 52, and optionally a catheter insertion fin 56. Catheter adaptor 50 is usually constructed from a single mold with catheter cannula 52 attached to the proximal end of catheter adaptor 50. An opening 58 runs axially down the center of catheter adaptor 50 and joins with the distal end of catheter cannula 52, creating a continuous fluid passage through catheter adaptor 50 and cannula 52.

In one embodiment, catheter 54 has a catheter insertion fin 56 used to attach a medication container once catheter cannula 52 is positioned within the patient's blood vessel. Catheter insertion fin 56 has an inlet 66 which unites with opening 58 in catheter adaptor 50. Thus, medication, blood, or fluid in the container travels down inlet 66, through opening 58 and cannula 52, and into the patient's blood vessel. In embodiments that include a catheter insertion fin 56, a blood seal 68 is preferably disposed within opening 58 in catheter adaptor 50. Blood seal 68 is positioned distally from the intersection of inlet 66 and opening 58. When catheter adaptor 50 is engaged with needle puller 30, introducer needle 38 passes through blood seal 68. Once catheter cannula 52 is in position within the patient's blood vessel and introducer needle 38 is removed, blood seal 68 seals off opening 58 preventing blood or medication from exiting the distal end of opening 58.

With continued reference to FIG. 1, the distal end of catheter adaptor 50 is designed to frictionally engage cavity 34 and stem 36 located on the proximal face of needle puller body 32. As such, the diameter of opening 58, at the distal end of catheter adaptor 50 is slightly larger than the outer diameter of stem 36, and the outer diameter of the distal end of catheter adaptor 50 is slightly smaller than the outer diameter of cavity 34.

The distal end of catheter adaptor 50 has a latch groove 60. Latch groove 60 carves out a latch groove lip 62. As illustrated in FIG. 1, latch groove 60 and latch groove lip 62 extend around the entire circumference of catheter adaptor 50. It will be appreciated by one skilled in the art, however, that latch groove 60 and latch groove lip 62 need not extend the entire circumference of catheter adaptor 50. For example, latch grooves 60 may be configured with at least one straight edge so, when catheter adaptor 50 and needle puller 30 are engaged, catheter adaptor 50 cannot freely rotate relative to needle puller 30. The width of latch groove 60 is approximately that of channels 40 of needle puller body 32.

In addition, catheter adaptor 50 has a push tab 64. Push bar 64 provides a surface the clinician can grip and apply resistance against as introducer needle 38 is being inserted into the blood vessel of the patient. Push bar 64 is also used by the clinician to detach catheter adaptor 50 from needle puller 30 and advancing catheter cannula 52 into the patient's blood vessel.

FIGS. 3 and 4 illustrate the present invention when needle puller 30 and catheter adaptor 50 are attached, and yoke latch 10 is engaged. When needle puller 30 and catheter adaptor 50 are attached, the distal end of catheter adaptor 50 is disposed within cavity 34 and stem 36 is frictionally engaged with the distal end of opening 58 in catheter adaptor 50. In this configuration, channels 40 are vertically aligned with latch groove 60 such that latch groove lip 62 is flush with the distal edges of channels 40. Further, prongs 14 rest only partially within channels 40 and push bar 12 is elevated above needle puller body 32. As best illustrated in FIG. 4, locking tabs 16 are in contact with abutments 46 and protrude the outer diameter of cavity 34, overlapping latch groove lip 62 of catheter adaptor 50. When locking tabs 16 overlap latch groove lip 62, catheter adaptor 50 is securely coupled to needle plunger 32 and catheter adaptor 50 cannot move proximally relative to needle puller 30.

In practice, the vascular access device 100 will usually be provided with needle puller 30 frictionally engaged to catheter adaptor 50. In the event they are not engaged, the clinician engages needle puller 30 to catheter adaptor 50 by inserting stem 36 of needle puller 30 into the distal end of opening 58 of catheter adaptor 50 until latch groove 60 is vertically aligned with channels 40. Once aligned, the clinician pulls up on push bar 12 until locking tabs 16 come into contact with abutments 46 and yoke latch 10 cannot be raised further. The relative widths of locking tabs 16 and latch groove 60 are such that they frictionally engage and maintain yoke latch 10 elevated and in an engaged position. Needle puller 30 and catheter adaptor 50 are now coupled and vascular access device 100 is ready for use.

With yoke latch 10 engaged, the clinician first inserts introducer needle 38 into the patient's blood vessel. Because needle puller 30 and catheter adaptor 50 are securely coupled, the clinician can grip vascular access device 100 by catheter adaptor 50. Once introducer needle 38 has been inserted into the patient's blood vessel, the clinician depresses push bar 12, disengaging yoke latch 10. The clinician then detaches catheter adaptor 50 from needle puller 30 by applying slight pressure against push tab 64 of catheter adaptor 50. Catheter cannula 52 of catheter adaptor 50 is then inserted into the patient's blood vessel by sliding it along introducer needle 38. While holding catheter adaptor 50 in place, the clinician grips needle puller 30 and slowly removes introducer needle 38 from the patient's blood vessel. As introducer needle 38 is removed, blood seal 68, seals off the distal end of opening 58 in catheter adaptor 50. Finally, medication and other fluids can be attached to catheter insertion fin 56 and administered to the patient.

In short, the present invention overcomes significant limitations in the art. The present invention provides a yoke latch which couples needle pullers to catheters. Therefore, unlike prior art vascular access devices, a clinician can grip the vascular access device by the catheter adaptor or cannula for better control in situations where the patient's blood vessel is small, deeply buried, or otherwise difficult to locate and puncture. Moreover, only one hand is required to disengage the yoke latch, uncouple the needle puller and remove the introducer needle from the patient's blood vessel. Accordingly, the present invention is a significant advancement in the art of vascular access devices.

What is claimed and desired to be secured by United States Letters Patent is:

1. A medical device, comprising:
    a needle device having a first end;
    a catheter adapter having a first end adjacent to the first end of the needle device;
    a latch movably disposed on the needle device between a first position and a second position, wherein when the latch is in the first position the latch engages the catheter adapter to prevent movement of the catheter adapter longitudinally away from the first end of the needle device and when the latch is in the second position the catheter adapter is free to move longitudinally away from the first end of the needle device wherein the latch comprises a horseshoe shape push bar, at least one prong extending from the push bar and at least one locking tab attached to the prong.

2. The medical device of claim 1 wherein the first end of the needle device defines a cavity for receiving the first end of the catheter adapter.

3. The medical device of claim 1 wherein the catheter adapter defines a groove adjacent to the first end of the catheter adapter for receiving the at least one prong.

* * * * *